(12) United States Patent
Huang et al.

(10) Patent No.: US 7,686,777 B2
(45) Date of Patent: Mar. 30, 2010

(54) PLASMA LIPIDS IN-VITRO FILTERING METHOD AND APPARATUS

(75) Inventors: Heping Huang, Shanghai (CN); Siukwan Chang, Shanghai (CN)

(73) Assignee: Shanghai Jiangxia Blood Technology Co., Ltd., Shanghai (CN)

( * ) Notice: Subject to any disclaimer, the term of this patent is extended or adjusted under 35 U.S.C. 154(b) by 0 days.

(21) Appl. No.: 10/599,708

(22) PCT Filed: Feb. 28, 2005

(86) PCT No.: PCT/CN2005/000239

§ 371 (c)(1),
(2), (4) Date: Jul. 27, 2007

(87) PCT Pub. No.: WO2005/097231

PCT Pub. Date: Oct. 20, 2005

(65) Prior Publication Data

US 2008/0058694 A1     Mar. 6, 2008

(30) Foreign Application Priority Data

Apr. 6, 2004 (CN) .................. 2004 2 0021636 U

(51) Int. Cl.
*A61M 37/00* (2006.01)
*A61M 1/00* (2006.01)
*B01D 63/00* (2006.01)
*C02F 1/44* (2006.01)
*B01D 61/00* (2006.01)

(52) U.S. Cl. .............. 604/5.03; 604/5.01; 604/6.02; 604/6.04; 604/6.06; 604/6.09; 604/6.11; 604/6.13; 604/6.15; 210/321.64; 210/321.6; 210/634; 210/644; 210/649; 210/650; 210/651; 422/44; 422/48

(58) Field of Classification Search .......... 209/583, 209/522, 552; 198/475.1, 370.05; 604/5.01, 604/5.03, 6.02, 6.04, 6.05, 6.06, 6.09, 6.11, 604/6.13, 6.15; 210/321.64, 321.6, 634, 210/644, 645, 646, 649, 650, 651; 422/44, 422/48; 436/71

See application file for complete search history.

(56) References Cited

U.S. PATENT DOCUMENTS

| | | | | | |
|---|---|---|---|---|---|
| 4,350,156 | A | * | 9/1982 | Malchesky et al. | 604/6.04 |
| 4,781,871 | A | * | 11/1988 | West et al. | 264/4.3 |
| 4,895,558 | A | * | 1/1990 | Cham | 604/5.03 |
| 4,908,354 | A | * | 3/1990 | Seidel et al. | 514/21 |
| 4,923,439 | A | * | 5/1990 | Seidel et al. | 604/5.03 |
| 5,141,493 | A | * | 8/1992 | Jacobsen et al. | 604/29 |
| 5,152,743 | A | * | 10/1992 | Gorsuch et al. | 604/6.09 |
| 5,252,222 | A | * | 10/1993 | Matkovich et al. | 210/650 |
| 5,348,533 | A | * | 9/1994 | Papillon et al. | 604/6.07 |
| 5,401,466 | A | * | 3/1995 | Foltz et al. | 422/56 |
| 5,679,260 | A | * | 10/1997 | Boos et al. | 210/723 |
| 5,744,038 | A | * | 4/1998 | Cham | 210/634 |
| 5,776,091 | A | * | 7/1998 | Brugger et al. | 604/6.1 |

(Continued)

*Primary Examiner*—Leslie R Deak
*Assistant Examiner*—Adam Marcetich

(57) ABSTRACT

An in-vitro blood plasma lipids filtering method includes the following steps: separating out the blood plasma from the blood collection; flushing a filtering device with saline solution; controlling the pressure of the separated blood plasma; passing the blood plasma to the filtering device for filtering out lipids; controlling the temperature of the filtered blood plasma; and feeding the blood plasma back to the blood. The method is clearly effective and accurate, quick response indication, securer and safer, more tolerant, and the treatment time is short.

12 Claims, 1 Drawing Sheet

U.S. PATENT DOCUMENTS

| | | | |
|---|---|---|---|
| 5,865,785 A * | 2/1999 | Bischof | 604/6.03 |
| 5,919,369 A * | 7/1999 | Ash | 210/645 |
| 6,264,623 B1 * | 7/2001 | Strahilevitz | 604/5.01 |
| 6,361,692 B1 * | 3/2002 | Bischof | 210/252 |
| 6,872,307 B2 * | 3/2005 | Bischof | 210/258 |
| 7,033,500 B2 * | 4/2006 | Bomberger et al. | 210/321.79 |
| 7,195,710 B2 * | 3/2007 | Bomberger et al. | 210/257.2 |
| 2003/0150809 A1 * | 8/2003 | Bomberger et al. | 210/651 |
| 2004/0050788 A1 * | 3/2004 | Gorsuch et al. | 210/645 |
| 2004/0124147 A1 * | 7/2004 | Fissell et al. | 210/650 |
| 2004/0256307 A1 * | 12/2004 | Bomberger et al. | 210/321.79 |
| 2005/0133450 A1 * | 6/2005 | Bomberger et al. | 210/645 |
| 2006/0000776 A1 * | 1/2006 | Bomberger et al. | 210/639 |

* cited by examiner

PLASMA LIPIDS IN-VITRO FILTERING METHOD AND APPARATUS

TECHNICAL FIELD OF THE INVENTION

The present invention relates to in-vitro blood plasma lipids filtering method and apparatus, and more particularly relates to in-vitro blood plasma lipids filtering method and apparatus.

BACKGROUND OF THE INVENTION

It is well known, with increasing living standards, the high-blood lipids has already become a universal disease. According to World Health Organization statistics, all over the world there are approximately 15 million mortality cases every year from cardio-cerebral-vascular diseases, which is more than 50% of the total mortality rate.

The blood lipids are referring to the fat content of the blood, usually referring to the cholesterol and triglyceride. The blood lipids are important to the human body growth, especially in cell formation and body metabolism. The hyperlipidemia is referring to the excessively high blood level of cholesterol (TC), the triglyceride (TG), or the low-density lipoprotein cholesterol (LDL-C), in modern medical terminology referred to as abnormal blood lipids.

The abnormal blood lipids lead to atherosclerosis, an important dangerous factor of coronary disease. Famous FRAMINGHAM studies proven that lowering TC 1% reduces 2% of CVE. Reducing TC and LDL-C is important in controlling and preventing coronary diseases. In brain infarction patients, patients with Blood Hypervisicosity Syndrome (HBS) formation rate reaches as high as 63.7%.

Regarding diseases caused as a result of high blood lipids, the drug treatment thus far has proven to be unsatisfying. At present, with biological technology progression, leading to the filtering method using in-vitro blood plasma to prevent and control diseases caused by high blood lipids (cholesterol, triglyceride, low-density lipoprotein and chyle-cholesterol). In-vitro blood plasma filtering method is gradually becoming the direction of research and development in biological and medical science.

In order to reduce blood lipids quickly, lipid reduction apparatus has already obtained clinical use. However, an apparatus of such kind usually uses physical chemistry method to carry on the lipid reduction process. Lipid reduction via lipid reducing apparatus is more effective and direct, in comparison with drug treatment to reduce blood plasma lipids. An apparatus of such kind is still unsatisfactory, and certainly has safety concerns.

At present, the main clinical use is a German apparatus, and this lipid reduction apparatus first treats the patient's blood plasma by a chemical process to adjust the PH value, and then filters the blood plasma lipids after the chemical precipitation process. Utilizing this apparatus to filter the blood plasma lipids usually takes three hours to complete. Moreover, after two filtering processes, the lipid reduction effect is also reduced to only 30%-50%. Especially, after chemical processing, the hemoglutination in blood plasma may be damaged or lost as a result. In addition, this apparatus is currently very expensive, and the operational procedure is complex.

SUMMARY OF THE INVENTION

The present invention provides an in-vitro blood plasma lipids filtering method, which overcomes the above-mentioned technical difficulty and insufficiency.

An objective of the present invention is to resolve and provide a technology which is more direct and effective, and also provides a safe blood plasma lipids removal procedure.

In accordance with an aspect of the present invention, the present invention provides an in-vitro blood plasma lipids filtering method, comprising the following steps: collecting blood by a blood collecting device; separating out blood plasma from the collected blood from a patient by a blood separating device connected to the blood collecting device, wherein the separated blood plasma enters a pre-filtered blood plasma bag which includes an automatic weight or volume detector device for transmitting a signal that triggers a stop response to the blood separating device or the blood collecting device when the pre-filtered blood plasma bag is full; flushing a filtering device with saline solution; flushing a blood plasma lipids filtering device connected to the pressure control device with saline solution from a saline solution treatment bag connected to an outlet of the pre-filtered blood plasma bag, wherein the flushed saline solution from the blood plasma lipids filtering device flows into a waste saline solution bag connected to the blood plasma lipids filtering device; controlling peristalsis and pressure of the separated blood plasma by a peristaltic pump and a pressure control device connected to the pre-filtered blood plasma bag; passing the separated blood plasma through to the filtering device for filtering out lipids of the separated blood plasma; collecting the filtered blood plasma by a post-filtered blood plasma bag connected to the blood plasma lipids filtering device; controlling the temperature of the filtered blood plasma from the post-filtered blood plasma bag by a temperature control device connected to the post-filtered blood plasma bag; and feeding the filtered blood plasma back into the blood of the patient by a blood plasma feedback device connected to the temperature control device.

During the filtering process, the collected blood is gradually treated and separated out. Each separation separates out about 150-250 milliliters of the blood plasma. The blood plasma passes through the filtering device about 20-30 milliliters every minute. In the above-described filtering device, pressure is controlled below 60KPa. Adding heat to the blood plasma and the temperature is just about equal to the body temperature.

The above described blood plasma lipids filtering device comprises three thin films or membrane, wherein at least a first film may be a membrane which has filter aperture pores of about 0.3 to 0.65 microns and comprises a lipid absorptive material; a second film is a membrane which has filter aperture pores of about 0.3 microns; and a third film is a membrane which has filter aperture pores of about 0.2 microns and is made of nylon as the base material. In between the second and third thin films, there is one or multiple layers of the first thin film. The lipid absorptive material used is the silicon oxide pellets.

Another objective of the present invention is to provide an in-vitro plasma lipids filtering apparatus, which is more direct and effective, and also provides a safe blood plasma lipids removal procedure.

In accordance with an aspect of the present invention, the present invention provides an in-vitro blood plasma lipids filtering apparatus, comprising: a blood collecting device for collecting blood from a patient; a blood separating device connected to the blood collecting device for separating blood plasma from the collected blood; a pre-filtered blood plasma bag connected to the blood separating device and including an automatic weight or volume detector device for transmitting a signal that triggers a stop response to the blood separating device or the blood collecting device when the pre-filtered blood plasma bag is full; a peristaltic pump connected to the pre-filtered blood plasma bag for producing flowing power for the separated blood plasma; a pressure control device connected to the peristaltic pump for controlling the pressure of the separated blood plasma by adjusting the rotational speed of the peristaltic pump; a blood plasma lipids filtering device connected to the pressure control device for filtering out lipids of the separated blood plasma; a post-filtered blood plasma bag connected to the blood plasma lipids filtering device for collecting the filtered blood plasma; a temperature control device connected to the post-filtered blood plasma bag for controlling the temperature of the filtered blood plasma from the post-filtered blood plasma bag; as well as a blood plasma feedback device connected to the temperature control device for feeding the filtered blood plasma back into the blood of the patient. These devices are connected via pipelines and/or tubes, and the pipelines and tubes are also connected with the peristaltic pump. In addition, the pressure control device and the temperature control device are installed among the pipelines and tubes. The in-vitro blood plasma lipids filtering device also includes a saline solution treatment bag and a waste saline solution bag. The saline solution treatment bag is connected to an outlet of the pre-filtered blood plasma bag for providing saline solution to flush the blood plasma lipids filtering device before the blood lipids filtering device filters out lipids of the separated blood plasma, and the waste saline solution bag is connected to an inlet of the post-filtered blood plasma bag for collecting the flushed saline solution from the blood plasma lipids filtering device during flushing the blood plasma lipids filtering device.

The above-mentioned pre-filtered blood plasma bag includes the automatic weight or volume detector device for transmitting a signal when the blood plasma bag is full to the blood separating device or the blood collecting device, thereby triggering a stop response. The volume of the pre-filtered blood plasma bag is about 150-250 milliliters.

The above-mentioned pressure control device can read out the current pressure inside the pipeline tube between the peristaltic pump and the blood plasma lipids filtering device. The pressure control device controls the pressure to be below 60KPa. The rotational speed of the peristaltic pump is controlled to maintain a flow rate of the blood plasma at about 20-30 milliliters every minute.

The above-mentioned temperature control device is installed within the filtering apparatus, and connected between the post-filtered blood plasma bag and the blood plasma feedback device, so that the highest heating temperature is controlled at 38° C.

The above described blood plasma lipids filtering device comprises three thin films or membrane, wherein at least a first film may be a membrane which has filter aperture pores of about 0.3 to 0.65 microns and comprises a lipid absorptive material; a second film is a type of membrane which has filter aperture pores of about 0.3 microns; and a third film is a membrane which has filter aperture pores of about 0.2 microns and is made of nylon as the base material. In between the second and third thin films, there is one or multiple layers of the first thin film. The lipid absorptive material used is the silicon oxide pellets.

The present invention can remove the blood lipids, and thus is suitable to use in cases of high blood lipids diseases that are not suitable for drug treatment, such as in high cholesterol blood level, hypertriglyceridemia, high-and-low-density lipoproteinemia, Blood Hypervisicosity Syndrome (BHS), and so on. The present invention is obviously effective in removing blood fibrinogen, preventing stroke, and reducing blood viscosity. The present invention can remove about 50% of blood lipids in one time filtering, and moreover, may be repeatedly carried out numerous times.

The present invention utilizes the pure physical affinity with the natural adsorption method; therefore, the present invention is safer, securer, and more tolerant. During treatment, patients generally have not shown obvious discomfort. In addition, the treatment time is short and patients usually spend approximately two hours per treatment. Moreover, the operational procedure is simple and requires minimal supervision of specialists or special trainings.

BRIEF DESCRIPTION OF THE DRAWINGS

A detailed description will be given with respect to a preferred embodiment of the present invention and the best mode for carrying out the present invention for further explanation to this invention with reference to the sole drawing, FIG. 1, which is a schematic illustration showing an implementation example of an in-vitro blood plasma lipids filtering apparatus of the present invention.

DETAILED DESCRIPTION OF THE PREFERRED EMBODIMENT AND THE BEST MODE FOR CARRYING OUT THE PRESENT INVENTION

The present invention will be further described in details in conjunction with the accompanying drawing.

Figure 1:
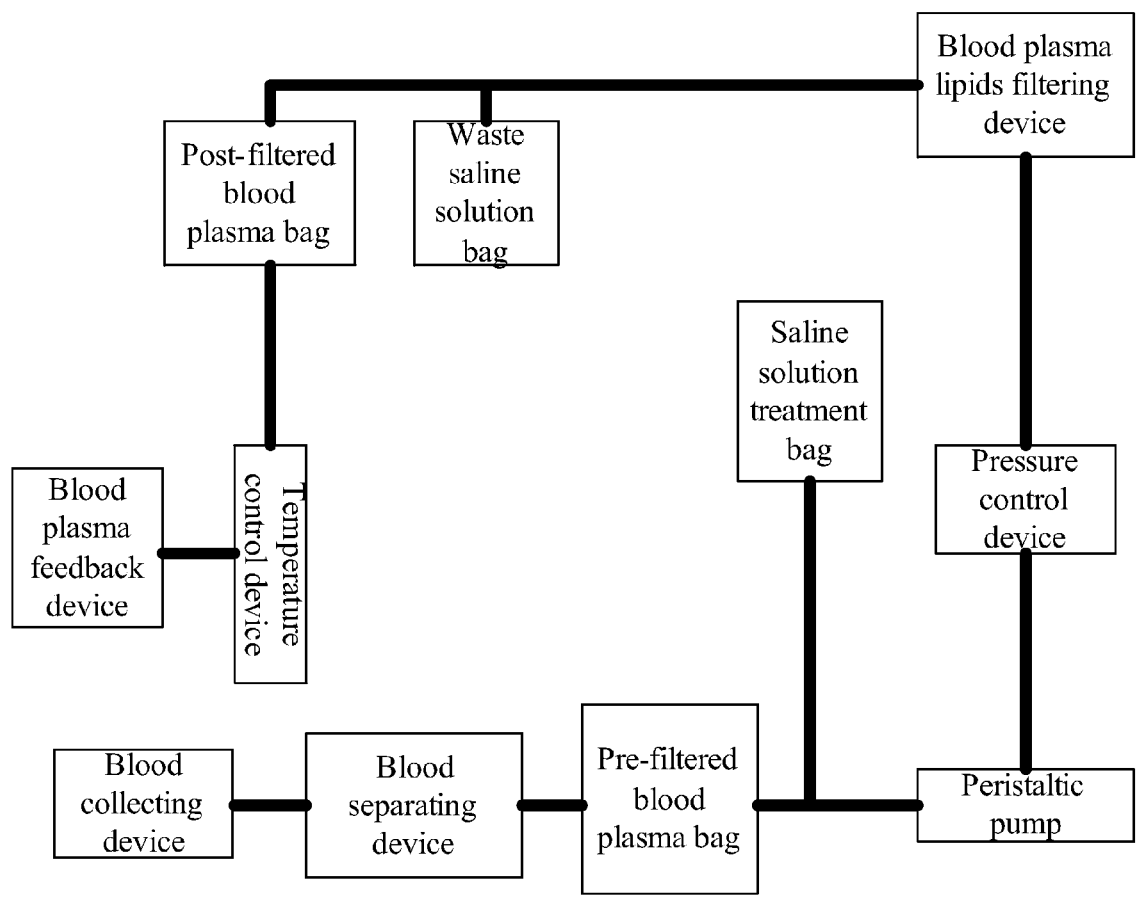
Referring to FIG. 1, which is a schematic illustration showing an implementation example of an in-vitro blood plasma lipids filtering apparatus of the present invention that a blood separating device is first employed to carry out a centrifugal separation method and separates the blood plasma from the blood collected by the blood collecting device; other cellular components (i.e. blood cells) are feedback to the patients in a feedback loop. The separated blood plasma enters a pre-filtered blood plasma bag, and a saline solution treatment bag for pre-treating a blood plasma lipids filtering device and tubes is connected to the blood plasma lipids filtering device at an outlet of the pre-filtered blood plasma bag.

The pre-treatment saline solution or separated blood plasma flows through the pipeline tubes to a peristaltic pump. The peristaltic pump provides power and pressure for the in-vitro blood plasma lipids filtering apparatus. An end terminal of the peristaltic pump has an adjustable pressure control to adjust and control pressure for ensuring a safer and comfortable treatment process. Then the pipeline tube is connected to the blood plasma lipids filtering device, and filter membrane of the blood plasma lipids filtering device is evenly distributed with massive functional particles. Centrifuged mixed-particles blood plasma flows through the filter membrane so that TC, TG, LDL and so on, are firmly attracted and attached on the filter membrane. Thereby, the unclouded, thus purified blood plasma flows out of the blood plasma lipids filtering device, and enters into a post-filtered blood plasma bag through the pipeline tube. An inlet of the post-filtered blood plasma bag is connected with a pipeline tube to a waste saline solution bag. During saline solution treatment, the pipeline tube to the post-filtered blood plasma bag is shut-off, so that post-filtered blood plasma is not mixed with the saline solution, and the treated saline solution flows to the waste saline solution bag. During the blood filtering process, shutting-off the pipeline to the waste saline solution bag, so as to ensure that the treated blood plasma flows to the post-filtered blood plasma bag. The blood plasma passes through a temperature control device to maintain a constant temperature of the treated blood plasma. The temperature-controlled blood plasma is then fed back to the body via a blood plasma feedback device.

In the above-mentioned device, the blood colleting device collects the blood and also allows the blood cellular components (i.e. blood cells) to be fed back in a loop. Therefore the device may be a general blood-collecting device, or the device may be specially designed double-barrel single-needle device. Certainly, the device may be designed to independently draw blood and with the feature of feedback pipeline tube and needle. However, a device like such will require that the patients to be inserted twice with needles, and presumably will increase pain on the patients.

The separated blood plasma flows into a pre-filtered blood plasma bag. The pre-filtered blood plasma bag has a certain volume or weight, so that when the blood plasma inside the blood plasma bag achieves a certain volume or weight, the blood separating device and the blood collecting device will stop. In some implementation examples, the blood plasma bag has an automatic volume or weight detection device, which transmits a signal when the blood plasma in the pre-filtered blood plasma bag is full, so that the blood separating device and the blood collecting device are triggered to shut-off. Generally, a typical volume of a blood plasma bag is about 200 milliliters. The said volume satisfies filtering efficiency and ensures that patients feels comfortable, and causes no damage to danger to the patients.

The present invention also has a saline solution treatment device, the saline solution treatment bag parallel with the pre-filtered blood plasma bag are connected to the blood plasma lipids filtering device. Moreover, just prior to the entrance of the post-filtered blood plasma bag, there exists a pipeline tube connecting to the waste saline solution bag. Before the start of the filtering apparatus, the pre-filtered blood plasma bag is shut-off, the saline solution inside the saline solution treatment bag flushes the pipeline tube and the blood plasma lipids filtering device, and the flushed saline solution enters the waste saline solution bag. Closure of the saline solution treatment bag is made after the flushing is completed. The pre-filtered blood plasma bag is open to allow the separated blood plasma to flow into pipeline tube. The flushing of saline solution is due to the following considerations. First, typical medical devices and pipeline tubes are disinfected daily or after each use. These disinfectants, such as Oxirane, are generally harmful to the human body, and can remain in the pipeline tube in varying degrees. The saline solution treatment can wash off these harmful residues. Next, the saline solution treatment can be used to check the system's seal-proof quality, in order to guard against leakage occurring during process. Again, after the closure of the saline solution bag, there may be saline solution remaining in the pipeline tube and the apparatus, and the residual saline solution can be used to supplement patient's blood capacity. After post-filtration process, the blood plasma is exchanged to prevent the loss of blood plasma. The saline solution treatment bag and the waste saline solution bag may also be installed in other parts of the filtering apparatus that can totally wash-out the pipeline tube and device.

Blood plasma in the pre-filtered blood plasma bag flows to the peristaltic pump, and the peristaltic pump provides the pipeline tube with power for liquid movement. In the back of the peristaltic pump, there is a pressure control device, which can read out the current pipeline tube pressure. In some implementation examples, the pressure control device may also adjust the rotational speed of the peristaltic pump. The rotational speed of the peristaltic pump produces flowing power for the blood plasma, and the blood plasma later during screening procedure is subject to resistance in the blood plasma lipids filtering device and then generates pressure. The pressure, if too large, may harm the filtering apparatus, and simultaneously can also cause the patient to feel ill. However, the rotational speed of the peristaltic pump, if too slow, causes the blood plasma flow speed to be slow, and can lead to lengthening the filtration time. Numerous implementation examples prove that when the speed of flow is about 20-30 milliliters per minute, the lipid reduction is more effective. Therefore, general rotational speed of the peristaltic pump is set in advance at this level. However, due to the fact that some patients' blood plasma density is higher, and may be more difficult to pass the blood plasma lipids filtering device, and thus may induce tremendous pressure. When the pressure achieves a level which could possibly harm the filtering apparatus or make the patients feel ill, the pressure control device will indicate this pressure value, and the monitoring staff can reduce the rotational speed of the peristaltic pump to reduce pressure. When the pressure control device can control the rotational speed of the peristaltic pump, the filtering process will be able to complete automatically. Therefore, the pressure control can be done by a simple pressure gauge or an automatic velocity regulation system comprising a pressure sensory device and speed controlled peristaltic pump. In an example of the present invention, the pressure marginal value is about 60KPa. Because pressure production and density level of blood plasma are related, through monitoring the reading value on the pressure control device, patient's blood density and condition may be determined.

The blood plasma, after peristaltic pump process, enters the blood plasma lipids filtering device. The blood plasma lipids filtering device comprises multi-layers of thin film membranes, of which a first film may be a membrane which has filter aperture pores of about 0.3 to 0.65 microns and comprises a lipid absorptive material. The first membrane may attract the fatty contents in the blood plasma, and the lipid absorptive material may be of the silicon oxide pellet. In addition, the first membrane filters out other impure particles that are bigger than the filter pores. A second film is a membrane which has filter aperture pores of about 0.3 microns. The second membrane can filter out bacterium and chyle-lipoprotein, because bacterium and chyle-lipoprotein have diameters greater than 0.3 microns. A third film is a membrane which has filter aperture pores of about 0.2 microns and is made of nylon as the base material. The third membrane filters out any and all foreign particles generated from the first and second filtering processes, such matters like thin film wood-pulp material or adsorptive particles.

The use and number of membrane layers depend on the adsorptive ability and the volume of blood to be filtered must be taken into consideration together. That is, if one layer is insufficient, and multiple layers may be considered to use in stead. In addition, other lipid adsorptive membranes may be placed in between the above-mentioned second and third membranes to make up the insufficiency of the first, second, or third membranes. For example, at least one additional first film is further interposed between the second and third films.

The blood plasma, after filtering process, flows into the post-filtered blood plasma bag and further goes through the blood plasma feedback device and is fed back to the patients. A temperature control device located on the pipeline tube between the post-filtered blood plasma bag and the blood plasma feedback device maintains that the blood plasma is at a temperature approximately close to the body temperature. The advantage is that patients are as close to natural condition as possible and thus are comfortable. This temperature control device may be a heating plate with the highest heating temperature controlled at about 38° C. The temperature control device may be placed anywhere in the pipeline tube or the device which is suitable for heating. The optimal location of the hot plate is suggested in the filtering device.

It is to be understood, however, that even though numerous characteristics and advantages of the present invention have been set forth in the foregoing description, together with details of the method and function of the invention, the disclosure is illustrative only, various modifications and changes may be made by persons skilled in this art, especially in arrangement of parts within the principles of the invention to the full extent indicated by the broad general meaning of the terms in which the appended claims are expressed. It is intended that the present invention should not be limited to the particular forms, and that all modifications and changes which maintain the spirit and realm of the present invention are within the scope as defined in the appended claims.

What is claimed is:

1. An in-vitro blood plasma lipids filtering method, comprising the following steps:

collecting blood from a patient by a blood collecting device;

separating blood plasma from the collected blood by a blood separating device connected to the blood collecting device, wherein the separated blood plasma enters a pre-filtered blood plasma bag which includes an automatic weight or volume detection device for transmitting a signal that triggers a stop response to the blood separating device or the blood collecting device when the pre-filtered blood plasma bag is full;

flushing a blood plasma lipids filtering device connected to the pressure control device with saline solution from a saline solution treatment bag connected to an outlet of the pre-filtered blood plasma bag, wherein the flushed saline solution from the blood plasma lipids filtering device flows into a waste saline solution bag connected to the blood plasma lipids filtering device;

controlling pressure of the separated blood plasma from the pre-filtered blood plasma bag by a pressure control device connected to the pre-filtered blood plasma bag;

passing the separated blood plasma through the blood plasma lipids filtering device for filtering out lipids of the separated blood plasma, wherein the blood plasma lipids filtering device comprises multi-layers of thin film membranes of which at least a first film is a membrane excluding hollow fibers of hollow fiber contactor (HFC) and having filter aperture pores of about 0.3 to 0.65 microns and comprises a lipid absorptive material for filtering out lipids of the separated blood plasma, a second film is a membrane that has filter aperture pores of about 0.3 microns for filtering out bacterium and chyle-lipoprotein, and a third film is a membrane that has filter aperture pore of about 0.2 microns and comprises nylon as a base material for filtering out foreign particles generated from the first and second filtering processes, wherein the foreign particles include thin film wood-pulp material or adsorptive particles, wherein at least one additional first film is further interposed between the second and third films, and wherein the lipid absorptive material of the first film and the additional first film comprises silicon oxide pellets;

collecting the filtered blood plasma by a post-filtered blood plasma bag connected to the blood plasma lipids filtering device;

controlling the temperature of the filtered blood plasma from the post-filtered blood plasma bag by a temperature control device connected to the post-filtered blood plasma bag; and feeding the filtered blood plasma back to the blood of the patient by a blood plasma feedback device connected to the temperature control device.

2. The method as claimed in claim 1, wherein the separating step comprises a stepwise separation process for separating the collected blood plasma from the blood collecting device at about 150-250 milliliters of the blood plasma each time.

3. The method as claimed in claim 1, wherein the separated blood plasma passes to the blood plasma lipids filtering device at a speed of 20-30 milliliters per minute, and the speed is controlled by a peristaltic pump connected to the pre-filtered blood plasma bag and the pressure control device.

4. The method as claimed in claim 1, wherein in the blood plasma lipids filtering device, the pressure is controlled below 60 KPa by the pressure control device.

5. The method as claimed in claim 1 further comprising a step of controlling the temperature of the filtered blood plasma from the post-filtered blood plasma bag approximately equal to body temperature by the temperature control device.

6. An in-vitro blood plasma lipids filtering apparatus comprising:

a blood collecting device for collecting blood from a patient;

a blood separating device connected to the blood collecting device for separating the blood plasma from the blood collected by the blood collecting device by centrifugal separation;

a pre-filtered blood plasma bag connected to the blood separating device and including an automatic weight or volume detection device for transmitting a signal that triggers a stop response to the blood separating device or the blood collecting device when the pre-filtered blood plasma bag is full;

a peristaltic pump connected to the pre-filtered blood plasma bag for producing flowing power for the separated blood plasma;

a pressure control device connected to the peristaltic pump for controlling the pressure of the separated blood plasma by adjusting the rotational speed of the peristaltic pump;

a blood lipids filtering device connected to the pressure control device for receives the separated blood plasma and filtering out lipids of the separated blood plasma, wherein the blood plasma lipids filtering device comprises multi-layers of thin film membranes of which at least a first film is a membrane excluding hollow fibers of hollow fiber contactor (HFC) and having filter aperture pores of about 0.3 to 0.65 microns and comprises a lipid absorptive material for filtering out lipids of the separated blood plasma, a second film is a membrane that has filter aperture pores of about 0.3 microns for filtering out bacterium and chyle-lipoprotein, and a third film is a membrane that has filter aperture pore of about 0.2 microns and comprises nylon as a base material for filtering out foreign particles generated from the first and second filtering processes, wherein the foreign particles include thin film wood-pulp material or adsorptive particles, wherein at least one additional first film is further interposed between the second and third films, and wherein the lipid absorptive material of the first film and the additional first film comprises silicon oxide pellets;

a post-filtered blood plasma bag connected to the blood plasma lipids filtering device for collecting the filtered blood plasma;

a temperature control device connected to the post-filtered blood plasma bag for controlling the temperature of the filtered blood plasma from the post-filtered blood plasma bag; and a blood plasma feedback device connected to the temperature control device for feeding the filtered blood plasma back into the blood of the patient;

the in-vitro blood plasma lipids filtering apparatus further comprising:

a saline solution treatment bag connected to an outlet of the pre-filtered blood plasma bag for providing saline solution to flush the blood plasma lipids filtering device before the blood lipids filtering device filters out lipids of the separated blood plasma; and a waste saline solution bag connected to an inlet of the post-filtered blood plasma bag for collecting the flushed saline solution from the blood plasma lipids filtering device during flushing the blood plasma lipids filtering device.

7. The in-vitro blood plasma lipids filtering apparatus as claimed in claim 6, wherein the pre-filtered blood plasma bag has a volume of about 150-250 milliliters.

8. The in-vitro blood plasma lipids filtering apparatus as claimed in claim 6, wherein the pressure control device indicates a current pressure value and can control the rotational speed of the peristaltic pump.

9. The in-vitro blood plasma lipids filtering apparatus as claimed in claim 6, wherein the peristaltic pump is controlled to have the rotational speed that induces a flow rate of the separated blood plasma at about 20-30 milliliters every minute.

10. The in-vitro blood plasma lipids filtering apparatus as claimed in claim 6, wherein the pressure control device controls the pressure to be below 60 KPa.

11. The in-vitro blood plasma lipids filtering apparatus as claimed in claim 6, wherein the temperature control device is used to maintain a constant temperature of the blood plasma.

12. The in-vitro blood plasma lipids filtering apparatus as claimed in claim 6, wherein the temperature control device is operable to have a highest heating temperature at 38° C.

* * * * *